(12) United States Patent
Babar et al.

(10) Patent No.: US 9,961,852 B2
(45) Date of Patent: May 8, 2018

(54) OAT VARIETY FL0720

(71) Applicant: University of Florida Research Foundation, Inc., Gainesville, FL (US)

(72) Inventors: Md Ali Babar, Gainesville, FL (US);
Ronald D. Barnett, Quincy, FL (US);
Ann R. Blount, Marianna, FL (US);
Stephen A. Harrison, Baton Rouge, LA (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 26 days.

(21) Appl. No.: 15/174,528

(22) Filed: Jun. 6, 2016

(65) Prior Publication Data

US 2017/0347602 A1 Dec. 7, 2017

(51) Int. Cl.
| | | |
|---|---|---|
| *A01H 5/10* | (2006.01) | |
| *A01H 5/00* | (2006.01) | |
| *A01H 1/02* | (2006.01) | |
| *C12N 15/82* | (2006.01) | |

(52) U.S. Cl.
CPC .............. *A01H 5/10* (2013.01); *A01H 1/02* (2013.01); *C12N 15/8241* (2013.01); *C12N 15/8245* (2013.01); *C12N 15/8247* (2013.01); *C12N 15/8251* (2013.01); *C12N 15/8271* (2013.01); *C12N 15/8274* (2013.01); *C12N 15/8275* (2013.01); *C12N 15/8277* (2013.01); *C12N 15/8278* (2013.01); *C12N 15/8279* (2013.01); *C12N 15/8286* (2013.01); *C12N 15/8289* (2013.01)

(58) Field of Classification Search
None
See application file for complete search history.

(56) References Cited

U.S. PATENT DOCUMENTS

2014/0304851 A1* 10/2014 Mochon ................ A01H 5/10
800/263

OTHER PUBLICATIONS

Babar et al., "FL720: New winter type crown rust resistance oat variety for dual purpose for Southeastern US," poster # 921, Crop Science Society of America, International Conference, Minneapolis, MN, Nov. 15-18, 2015.
Babar et al., "Breeder's Description — FL0720 Oats, A new full-season winter cultivar for forage, grain, cover, and wildlife food crop uses," accessed Aug. 15, 2016.
Coffman, "Oat history, identification and classification," Technical Bulletin 1516, United States Department of Agriculture, 1977.

* cited by examiner

*Primary Examiner* — Jason Deveau Rosen
(74) *Attorney, Agent, or Firm* — Dentons US LLP

(57) ABSTRACT

The invention provides oat seed and plants of the oat variety FL0720 that have resistance to crown rust. The invention further provides seed and plants of the oat variety FL0720 and progeny produced with at least one of these plants as a parent. The invention also relates to the plants, seeds, and tissue cultures of hybrid oat variety FL0720.

20 Claims, 2 Drawing Sheets

OAT VARIETY FL0720

BACKGROUND OF THE INVENTION

Field of the Invention

The present invention relates to the field of plant breeding and, more specifically, to the development of oat variety FL0720.

Background of the Invention

The goal of field crop breeding is to combine various desirable traits in a single variety/hybrid. Such desirable traits may include greater yield, resistance to insects, pests, or disease, tolerance to heat and drought, better agronomic qualities, higher nutritional value, growth rate, and fruit properties.

Breeding techniques take advantage of a plant's method of pollination. There are two general methods of pollination: a plant self-pollinates if pollen from one flower is transferred to the same or another flower of the same plant or plant variety. A plant cross-pollinates if pollen comes to it from a flower on a different plant.

One crop species that has been subject to such breeding programs and is of particular value is oat (*Avena sativa*). Oat is a cereal grain that is grown for its seed and is an important crop for human consumption, as well as a major source of animal feed.

While breeding efforts to date have provided a number of useful oat lines with beneficial traits, there remains a great need in the art for new lines with further improved traits. Such plants would benefit farmers and consumers alike by improving crop yields and/or quality, as well as providing increased dietary value for both humans and animals.

SUMMARY OF THE INVENTION

One aspect of the present invention relates to seed of the oat variety FL0720. The invention also relates to plants produced by growing the seed of the oat variety FL0720, as well as the derivatives of such plants. Further provided by the invention are plant parts, including cells, plant protoplasts, plant cells of a tissue culture from which oat plants can be regenerated, plant calli, plant clumps, and plant cells that are intact in plants or parts of plants, such as pollen, flowers, seeds, leaves, stems, and the like.

In a further aspect, the invention provides a composition comprising a seed of oat variety FL0720 comprised in plant seed growth media. In certain embodiments, the plant seed growth media is a soil or synthetic cultivation medium. In specific embodiments, the growth medium may be comprised in a container or may, for example, be soil in a field. Plant seed growth media are well known to those of skill in the art and include, but are in no way limited to, soil or synthetic cultivation medium.

Another aspect of the invention relates to a tissue culture of regenerable cells of the oat variety FL0720, as well as plants regenerated therefrom, wherein the regenerated oat plant is capable of expressing all of the morphological and physiological characteristics of a plant grown from the oat seed designated FL0720.

Yet another aspect of the current invention is an oat plant of the oat variety FL0720 further comprising a single locus conversion. In one embodiment, the oat plant is defined as comprising the single locus conversion and being otherwise capable of expressing all of the morphological and physiological characteristics of the oat variety FL0720. In particular embodiments of the invention, the single locus conversion may comprise a transgenic gene which has been introduced by genetic transformation into the oat variety FL0720 or a progenitor thereof. In still other embodiments of the invention, the single locus conversion may comprise a dominant or recessive allele. The locus conversion may confer potentially any trait upon the single locus converted plant, including, but not limited to, herbicide resistance, insect resistance, resistance to bacterial, fungal, or viral disease, male fertility or sterility, and improved nutritional quality.

Still yet another aspect of the invention relates to a first generation ($F_1$) hybrid oat seed produced by crossing a plant of the oat variety FL0720 to a second oat plant. Also included in the invention are the $F_1$ hybrid oat plants grown from the hybrid seed produced by crossing the oat variety FL0720 to a second oat plant. Still further included in the invention are the seeds of an $F_1$ hybrid plant produced with the oat variety FL0720 as one parent, the second generation ($F_2$) hybrid oat plant grown from the seed of the $F_1$ hybrid plant, and the seeds of the $F_2$ hybrid plant.

Still yet another aspect of the invention is a method of producing oat seeds comprising crossing a plant of the oat variety FL0720 to any second oat plant, including itself or another plant of the variety FL0720. In particular embodiments of the invention, the method of crossing comprises the steps of: (a) planting seeds of the oat variety FL0720; (b) cultivating oat plants resulting from said seeds until said plants bear flowers; (c) allowing fertilization of the flowers of said plants; and (d) harvesting seeds produced from said plants.

Still yet another aspect of the invention is a method of producing hybrid oat seeds comprising crossing the oat variety FL0720 to a second, distinct oat plant that is nonisogenic to the oat variety FL0720. In particular embodiments of the invention, the crossing comprises the steps of: (a) planting seeds of oat variety FL0720 and a second, distinct oat plant, (b) cultivating the oat plants grown from the seeds until the plants bear flowers; (c) cross pollinating a flower on one of the two plants with the pollen of the other plant, and (d) harvesting the seeds resulting from the cross pollinating.

Still yet another aspect of the invention is a method for developing an oat plant in an oat breeding program comprising: (a) obtaining an oat plant, or its parts, of the variety FL0720; and (b) employing said plant or parts as a source of breeding material using plant breeding techniques. In the method, the plant breeding techniques may be selected from the group consisting of recurrent selection, mass selection, bulk selection, backcrossing, pedigree breeding, genetic marker-assisted selection and genetic transformation. In certain embodiments of the invention, the oat plant of variety FL0720 may be used as the male or female parent.

Still yet another aspect of the invention is a method of producing an oat plant derived from the oat variety FL0720, the method comprising the steps of: (a) preparing a progeny plant derived from oat variety FL0720 by crossing a plant of the oat variety FL0720 with a second oat plant; and (b) crossing the progeny plant with itself or a second plant to produce a progeny plant of a subsequent generation which is derived from a plant of the oat variety FL0720. In one embodiment of the invention, the method further comprises: (c) crossing the progeny plant of a subsequent generation with itself or a second plant; and (d) repeating steps (b) and (c) for, in some embodiments, at least 2, 3, 4 or more additional generations to produce an inbred oat plant derived from the oat variety FL0720. Also provided by the invention is a plant produced by this and the other methods of the invention.

In another embodiment of the invention, the method of producing an oat plant derived from the oat variety FL0720 further comprises: (a) crossing the oat variety FL0720-derived oat plant with itself or another oat plant to yield additional oat variety FL0720-derived progeny oat seed; (b) growing the progeny oat seed of step (a) under plant growth conditions to yield additional oat variety FL0720-derived oat plants; and (c) repeating the crossing and growing steps of (a) and (b) to generate further oat variety FL0720-derived oat plants. In specific embodiments, steps (a) and (b) may be repeated at least 1, 2, 3, 4, or 5 or more times as desired. The invention still further provides an oat plant produced by this and the foregoing methods.

Figure 1:
FIG. 1—Shows oat varieties grown in a uniform Winter nursery. Oat variety FL0720 is shown in the front center.
Figure 2:
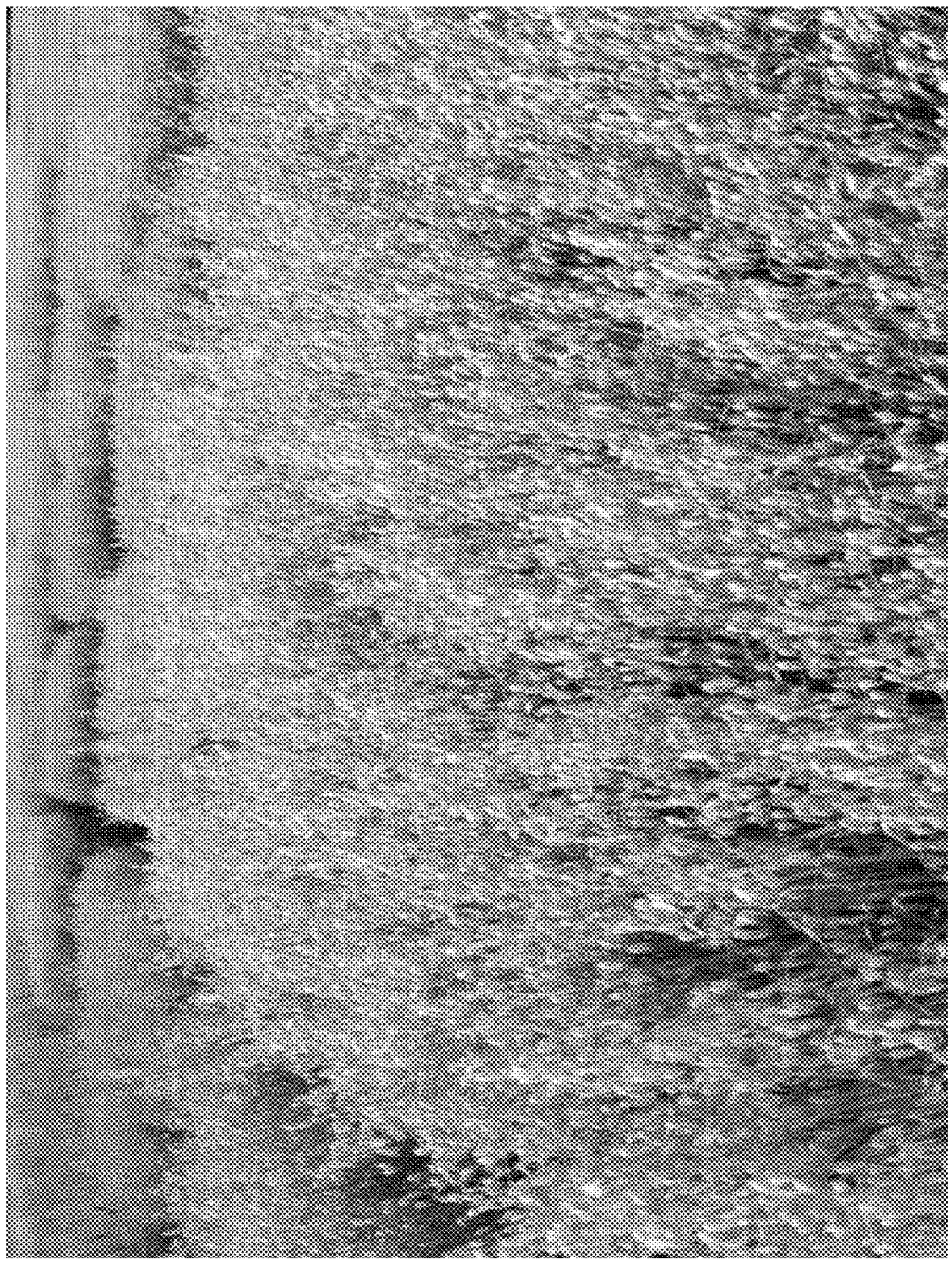
FIG. 2—Shows oat variety FL0720 grown in Winnsboro, La.

high early season forage yield with high grain yielding capacity compared to other commercial oat varieties in the southeastern United States. FL0720 has performed very well in both grain and forage trials and is broadly adapted to the southeastern United States. FL0720 is slightly less winter hardy than Horizon 201 and therefore may not perform as well as Horizon 201 in colder areas.

Oat variety FL0720 was derived from an initial 3-way cross as follows:

FL0206FSB-34-S1 (UFRGS 995088-3/LA9535D118-4)/FL06094 F1 (FL0016-H1 (Bw 3092/TX97C1168)/IL 3555)

UFRGS 995088-3=UFRGS 881971//Pc68/5*STARTER F4 advanced breeding line from Brazil

LA9535D118-4=TX91AB2965/5/C88D1547SEL'N:85-13/4/84-15/3/81-21//79-22*2/OMEGA

Bw 3092=Advance breeding line from Argentina

TX97C1168=UFRGS Q120101-4/TAMO386ERB/92SAT24-4

IL 3555=Barley Yellow Dwarf Virus (BYDV)-resistant germplasm release from the University of Illinois The FL0720 cross was made in spring of 2007 at NFREC greenhouse. Seventeen F1 seeds were obtained.

| | |
|---|---|
| Summer 2007 | 14 F1 seeds from cross 0720 were planted in row 389 in Aberdeen, Idaho. |
| Fall 2007 | 3 F1 seed were planted in the greenhouse as entry 509 in the spring 2008 crossing cycle. |
| Summer 2008 | F2 seed from 08GH509 and 07Ab389 were bulked and grown in F2 generation at Aberdeen as 08Ab row 304. Some seed was taken from 08Ab304 and used to enter FL0720 as an F3 bulk in the 09QION as entry 207. |
| 2009 | During 08-09 season, seed from 08Ab304 was planted in Oat Observations as plot no. 770 as an F3 bulk. |
| Spring 2009 | Seed was strip bulk harvested and grown as an F4 bulk in summer 09 Aberdeen Nursery as row 770. Forty panicles were individually harvested from 09 Aberdeen. |
| 2010 | The panicles harvested in spring 2009 were planted in the 2010 Oat Head Row Nursery as F5 rows. Six rows were harvested and designated as FL0720-R1 through FL0720-R6. |
| 2011 | Seed from head rows was grown in 2011 Oat Observation Plots (Table 2). |
| 2012 | Fl0720-R6 appeared promising and was entered in the 2012 Florida Elite Oat Nursery as an F7 line. 2012 was a very unusual growing season since it was very warm and many plots started jointing too soon and so most were injured by several cold snaps that we did have. A small preliminary increase of FL0720 was harvested in 2012. |
| 2013 | FL0720 was entered into the Regional USDA Uniform Winter Oat Nursery (Table 3). |

DETAILED DESCRIPTION OF THE INVENTION

The invention provides oat plants (*Avena sativa*) of variety FL0720, which exhibits elite agronomic traits that include resistance to crown rust. The variety represents an important advance over currently available oat varieties, which are typically susceptible to the pathogen causing crown rust.

Origin and Breeding History

FL0720 is a new winter oat variety that has considerable potential for forage, grain, conservation tillage, and wildlife purposes in the southern U.S. FL0720 was tested under the designation FL0720-R6 and is hereafter referred to as oat variety FL0720.

FL0720 is a good forage-type oat due to its full-season vigorous growth and high tillering capacity. It is tall in height, exhibits late maturity, has good grain yield, good test weight, yellow kernels, and has excellent crown rust resistance to the new strain of crown rust to which eastern oat varieties have been susceptible in Florida. FL0720 has a Physiological and Morphological Characteristics In accordance with one aspect of the present invention, there is provided a plant having the physiological and morphological characteristics of oat variety FL0720. A description of the physiological and morphological characteristics of oat variety FL0720 is presented in Table 1.

TABLE 1

Physiological and Morphological Characteristics of Oat Variety FL0720

| PHENOTYPE | Variety FL0720 |
|---|---|
| Species | *Avena sativa* |
| Use | Animal Feed |
| Growth habit | Semi Winter |
| Juvenile growth habit | Semi-prostrate |
| Maturity (50% flowering) (days) | 102 |
| No. of days maturing later than Horizon201 check variety | 2 |
| Maturity season | Mid-season |

TABLE 1-continued

Physiological and Morphological Characteristics of Oat Variety FL0720

| PHENOTYPE | Variety FL0720 |
|---|---|
| Plant height (cm) | 127 |
| No. of cm taller than Horizon201 check variety | 4 |
| STEM: | |
| Diameter | Medium |
| Hairiness at upper culm nodes | Hairless |
| Mature color | Yellow |
| LEAF: | |
| Carriage | Drooping |
| Color | Light green |
| Minimum leaf width (first leaf below the flag leaf) (mm) | 23 |
| Ligule | Present |
| Margin | Glabrous |
| Sheath | Hairless |
| HEAD: | |
| Panicle shape | Equilateral |
| Attachment of lower whorl of branches | First node |
| Panicle size | Medium |
| Panicle width | Midbroad |
| Panicle length (cm) | 22 |
| Number of branches | 3 |
| Number of whorls of branches | 8 |
| Position of branches | Drooping |
| RACHIS: | |
| Rachis | Erect |
| Second floret rachilla segment | Hairless |
| Second floret rachilla segment length (mm) | 2 |
| Second floret rachilla segment | Hairless |
| SPIKELET: | |
| Spikelet separation | By fracture |
| Floret separation | By basilfracture |
| Average number of florets per spikelet | 2.5 |
| GLUMES: | |
| Width (mm) | 6 |
| Length (mm) | 18 |
| Number of veins on glumes | 8 |
| Color | White |
| LEMMA: | |
| Length (mm) | 13 |
| Color | Yellow |
| Hairiness of dorsal surface | Hairless |
| AWN (FIRST FLORET): | |
| Occurrence | Absent |
| SEED: | |
| Basal hair | Absent |
| Grams per 1000 seeds | 38 |
| Groat weight, each (mg) | 31 |
| % Groat protein | 12.0 |
| % Groat Oil | 9.1 |
| DISEASE: | |
| Yellow Dwarf Virus | Resistant |
| Crown rust | Resistant to local races in southeast US |
| Stem rust | Moderately resistant to local races |

*These are typical values. Values may vary due to environment. Other values that are substantially equivalent are also within the scope of the invention.

Oat Variety FL0720 has been determined to be resistant to races of crown rust (CRS) that are general to the southeast United States. Variety FL0720 has also been determined to be resistant to Yellow Dwarf Virus and moderately resistant to Stem rust.

Oat variety FL0720 plants can be stably produced by growing the seed, such as that deposited with the ATCC.

Breeding Oat Varieties

One aspect of the present invention provides methods for crossing a plant of this invention with itself or a second plant and the seeds and plants produced by such methods. These methods can be used for propagation of an oat variety, such as variety FL0720, or can be used to produce hybrid oat seeds and the plants grown therefrom. For example, hybrid seeds may be produced by crossing a plant of the invention with a second oat parent line.

The development of further varieties using one or more starting varieties is well known in the art. In accordance with the invention, novel varieties may be created by crossing a starting line such as a plant of the invention followed by multiple generations of breeding according to such well-known methods. New varieties may be created by crossing with any second plant. In selecting such a second plant to cross for the purpose of developing novel lines, it may be desired to choose those plants which either themselves exhibit one or more selected desirable characteristics or which exhibit the desired characteristic(s) when in hybrid combination. Once initial crosses have been made, inbreeding and selection take place to produce new varieties. For development of a uniform line, often five or more generations of selfing and selection are involved.

Uniform lines of new varieties may also be developed by way of double-haploids. This technique allows the creation of true breeding lines without the need for multiple generations of selfing and selection. In this manner, true breeding lines can be produced in as little as one generation. Haploid embryos may be produced from microspores, pollen, anther cultures, or ovary cultures. The haploid embryos may then be doubled autonomously, or by chemical treatments (e.g. colchicine treatment). Alternatively, haploid embryos may be grown into haploid plants and treated to induce chromosome doubling. In either case, fertile homozygous plants are obtained. In accordance with the invention, any of such techniques may be used in connection with a plant provided herein and progeny thereof to achieve a homozygous line.

New varieties may be created, for example, by crossing a plant of the invention with any second plant and selection of progeny in various generations and/or by doubled haploid technology. In choosing a second plant to cross for the purpose of developing novel lines, it may be desired to choose those plants which either themselves exhibit one or more selected desirable characteristics or which exhibit the desired characteristic(s) in progeny. After one or more lines are crossed, true-breeding lines may be developed.

Backcrossing can also be used to improve an inbred plant. Backcrossing transfers a specific desirable trait from one inbred or non-inbred source to an inbred that lacks that trait. This can be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny are heterozygous for loci controlling the characteristic being transferred, but are like the superior parent for most or almost all other loci. The last backcross generation would be selfed to give pure breeding progeny for the trait being transferred.

The variety of the present invention is particularly well suited for the development of new varieties based on the elite nature of the genetic background of the variety. In selecting a second plant to cross with a plant of the invention for the purpose of developing novel oat lines, it will typically be preferred to choose those plants which either themselves exhibit one or more selected desirable characteristics or which exhibit the desired characteristic(s) when in hybrid combination. Examples of desirable characteristics may include, but are not limited to, nutritional content, seed yield, size, shape and uniformity, early maturity, disease resistance, herbicide tolerance, seedling vigor, adaptability for soil conditions, adaptability for climate conditions, for example heat and/or cold tolerance, and uniform plant height.

Performance Characteristics of Oat Variety FL0720

As described herein, oat variety FL0720 exhibits desirable agronomic traits, particularly resistance to crown rust. The results from an analysis of selected performance traits for the variety are presented below.

TABLE 2

2011 data from selected entries in Oat Observation Plots.

| Plot No. | Entry | Heading date | Yield Lbs Center row | Test Wt |
|---|---|---|---|---|
| 11O065 | FL0720-R5 | 91 | 1.14 | 32.0 |
| 11O066 | FL0720-R6 | 92 | 1.35 | 30.7 |
|  | Horizon 201 | 87 | 1.37 | 33.2 |
|  | Horizon 270 | 87 | 1.06 | 32.0 |
|  | Horizon 474 | 85 | 1.00 | 35.8 |
|  | LA99016 | 88 | 1.30 | 34.5 |
|  | LA99017 | 89 | 1.25 | 33.2 |

The Grain Yield and Test Weight data in the table above are the means of 9 locations (Prattville, Ala., Stuttgart, Ark., Quincy, Fla., 3 locations in NC, Ardmore, Okla., and College Station, Tex.). At two of the locations (Ardmore, Okla., and College Station, Tex.), FL0720 was the highest yielding among the 25 entries. FL0720 was seventh across all locations in grain yield and approximately 2 bu better than Horizon 201, which was ninth; and FL0720 had a test weight of 32.2 lbs/bu compared to 30.9 lbs/bu for Horizon 201. FL0720 had the same maturity as Horizon 201, and was 2 inches taller than H201, exhibited average resistance to Barley Yellow Dwarf Virus (BYDV), and had a crown rust rating of 0.3 compared to 5.2. Therefore, FL0720 exhibits outstanding crown rust resistance. It should be noted that all four of the commercially available varieties in the trial are very susceptible to crown rust. Crown rust ratings from the Buckthorn Nursery in St Paul, Minn. indicate that FL0720 indeed has strong resistance to crown rust. Individual genes for crown rust resistance in FL0720 are not known, however it is likely that FL0720 at least carries the Pc68 gene, since one line in its parentage had this gene. Data from Quincy, Fl., and Ardmore, Okla. are presented in Tables 3 and 4. It is interesting to note that when grown in Florida, variety FL0720 is 4 days later in heading than Horizon 201.

TABLE 3

2012-13 Uniform Winter Oat Trial, evaluated in six states. Mean across locations

| Entry | Name | Years in trial | Yield bu/a | rank | TW lb/bu | Heading Julian | Height in | Lodging 0-9 | BYDV 0-9 | Crown Rust 0-9 | Stem Rust 0-9 | Winter Stress 0-9 |
|---|---|---|---|---|---|---|---|---|---|---|---|---|
| 1 | Horizon 201 | 8 | 90.1 | 9 | 30.9 | 99.2 | 48.8 | 4.1 | 2.0 | 5.2 | 3.5 | 0.0 |
| 2 | LA99016 | 5 | 96.1 | 4 | 32.4 | 100.4 | 47.6 | 2.2 | 2.8 | 5.2 | 7.0 | 0.0 |
| 3 | Gerard 224 | 4 | 95.0 | 5 | 30.8 | 97.7 | 43.4 | 2.1 | 3.0 | 5.0 | 5.0 | 0.0 |
| 4 | TAMO 411 | 5 | 85.9 | 15 | 32.0 | 101.3 | 42.8 | 2.1 | 2.0 | 5.7 | 4.0 | 0.0 |
| 8 | FL0720-R6 | 1 | 92.5 | 7 | 32.2 | 99.8 | 50.8 | 2.8 | 2.8 | 0.3 | 3.5 | 0.0 |
|  | Mean |  | 86.1 |  | 32.3 | 97.7 | 43.3 | 2.9 | 2.8 | 4.2 | 4.6 | 0.3 |
|  | CV (%) |  | 22.6 |  | 6.7 | 3.3 | 6.0 | 61.3 |  |  |  | 146.2 |
|  | LSD (0.05) |  | 15.2 |  | 1.7 | 3.4 | 2.3 | 1.5 |  |  |  | 0.9 |
|  | $R^2$ |  | 0.86 |  | 0.85 | 0.95 | 0.88 | 0.73 |  |  |  | 0.94 |
|  | Number of locations |  | 9 |  | 9 | 5 | 7 | 8 | 2 | 2 | 2 | 2 |

Lodging: 0 = none, 9 = severe

CRUST: 0 = none, 9 = severe

ST RUST: 0 = none, 9 = severe

BYDV: 0 = none, 9 = severe

WS: 0 = none, 9 = severe

TABLE 4

USDA/ARS Uniform Winter Oat Yield Trial 2012-13.

| Entry | Designation | Yield bu/A | Yield Rank | TW lb/bu | Heading Julian | Height in. | Lodging 0-9 | BYDV 0-9 | Crown rust 0-9 |
|---|---|---|---|---|---|---|---|---|---|
| 1 | Horizon 201 | 31.5 | 12 | 25.2 | 97.5 | 56.6 | 7.8 | | 6.3 |
| 2 | LA99016 | 38.4 | 9 | 22.6 | 100.0 | 52.4 | 8.4 | | 6.3 |
| 3 | Gerard 224 | 21.3 | 19 | 15.2 | 99.5 | 50.6 | 8.4 | | 7.0 |
| 4 | TAMO 411 | 30.5 | 13 | 18.1 | 102.0 | 50.4 | 8.2 | | 6.3 |
| 8 | FL0720-R6 | 81.1 | 3 | 27.9 | 101.5 | 63.6 | 4.4 | | 0.0 |
| | Mean | 37.4 | | | 98.4 | 52.0 | 7.8 | | 5.1 |
| | CV (%) | 31.5 | | | 1.1 | 5.4 | 11.4 | | 18.8 |
| | LSD (0.05) | 16.6 | | | 2.2 | 3.5 | 1.1 | | 1.6 |

Lodging: 0 = none, 9 = severe
CRUST: 0 = none, 9 = severe
BYDV: 0 = none, 9 = severe

TABLE 5

USDA/ARS Uniform Winter Oat Yield Trial 2012-13, Ardmore, OK.

| entry | Name | lodging | winterkill | Test weight | Grain yield | Rank |
|---|---|---|---|---|---|---|
| 1 | Horizon 201 | 8.1 | 0.0 | 34.09 | 45.39 | 15 |
| 2 | LA99016 | 4.8 | -0.1 | 37.77 | 31.36 | 20 |
| 3 | Gerard 224 | 1.0 | 0.3 | 35.89 | 44.11 | 17 |
| 4 | TAMO 411 | 2.3 | 0.0 | 36.86 | 44.84 | 16 |
| 8 | FL0720-R6 | 5.3 | 0.6 | 33.65 | 86.15 | 1 |
| | CV | 37 | 36 | 2 | 16 | |
| | GRAND MEAN | 4.25 | 0.68 | 37.05 | 52.42 | |
| | Heritability | 0.66 | 0.99 | 0.87 | 0.73 | |
| | LSD | 2.66 | 0.41 | 1.20 | 13.93 | |
| | No. of Reps | 2 | 2 | 2 | 2 | |
| | R-Square | 0.84 | 0.99 | 0.94 | 0.87 | |

Lodging/Winterkill, 0 to 10 (severe)

In 2014, variety FL0720 was also included in official state variety trials in Louisiana, Texas, Georgia, and South Carolina, and several additional trials in Florida and Louisiana. A summary report (12 locations from 10 states) in presented in Table 6. Based on overall location data, FL0720 was ranked number 14 out of the 30 entries, but showed excellent crown rust resistance. Several of the locations for this regional trial were more temperate sites (AR, NC, MS, and North Texas locations) and do not truly represent the adaptation of the variety. When the southern locations were summarized (FL, LA, GA, AL, South Texas), FL720 ranked number 2, had 10 bu higher yield than Horizon 201, and also showed excellent crown rust resistance (Table 7). In addition, FL0720 exhibited 33 lbs/bu test weight compared with Horizon 201 with 31 lbs/bu. The data from Quincy, Fla., in a USDA regional nursery is presented in Table 8. Variety FL0720 showed a very impressive performance with 90 bu yield advantage and 11 lbs/bu higher test weight than Horizon 201. FL0720 also showed excellent crown rust resistance.

TABLE 6

2014 Summary report of the USDA regional nursery.

| Variety | Yield bu/ac | Rank | Test weight lbs/bu | rnk | Heading days of yr | Plant height in | Lodging 0-9 | Wint Surv % | Wint Stress (WS) 0-9 | Crown Rust 0-9 | Stem Rust 0-9 | BYDV 0-9 | Leafiness 0-9 |
|---|---|---|---|---|---|---|---|---|---|---|---|---|---|
| Horizon 201 | 117.4 | 2 | 31.6 | 24 | 99.7 | 44.5 | 4.2 | 59.8 | 3.3 | 5.0 | 1.0 | 1.0 | 3.3 |
| LA99016 | 87.2 | 20 | 33.5 | 8 | 96.7 | 38.1 | 5.3 | 31.7 | 6.1 | 0.0 | 3.0 | 0.7 | 4.3 |
| Gerard 224 | 115.5 | 3 | 32.6 | 16 | 100.2 | 37.5 | 2.3 | 53.7 | 2.7 | 7.0 | 5.0 | 1.5 | 4.2 |
| TAMO 411 | 114.7 | 5 | 34.5 | 3 | 101.3 | 38.1 | 2.2 | 69.9 | 2.6 | 7.0 | 6.0 | 0.4 | 4.3 |
| FL0720-R6 | 101.8 | 14 | 32.2 | 21 | 103.6 | 45.1 | 3.0 | 38.0 | 5.6 | 0.0 | 1.0 | 0.7 | 3.3 |
| Mean | 107.3 | | 32.9 | | 100.3 | 40.6 | 3.4 | 50.6 | 4.1 | 3.8 | 3.2 | 0.8 | 3.9 |

Showing data taken at 12 of 14 locations evaluated in 9 states (AL, AR, LA, LA, FL, GA, MS, NC, NC, OK, TX, TX).
Freeze Damage: 0-9, 0 = none, 9 = severe.
Leafy Score: 0-9, 3 = very leafy, 8 = not much leaf biomass. Average of several ratings.
Lodging: 0 = none, 9 = severe.
Crown Rust: 0 = none, 9 = severe.
Stem Rust: 0 = none, 9 = severe.
BYDV: 0 = none, 9 = severe.
WS: 0 = none, 9 = severe.

TABLE 7

2014 Nursery Means for Southern Locations.

| Variety | YLD bu/ac | Rank | Test weight lbs/bu | Heading days of yr | Plant height in | Lodging 0-9 | Winter stress (WS) 0-9 | Crown rust 0-9 | Stem rust 0-9 | BYDV 0-9 | Leafiness 0-9 |
|---|---|---|---|---|---|---|---|---|---|---|---|
| TX09CS1112 | 119 | 1 | 31 | 100 | 37 | 1.1 | 3.9 | 3.5 | 0.0 | 1.0 | 5.1 |
| FL0720-R6 | 113 | 2 | 33 | 105 | 50 | 3.0 | 5.6 | 0.0 | 1.0 | 0.7 | 3.3 |

TABLE 7-continued

2014 Nursery Means for Southern Locations.

| Variety | YLD bu/ac | Rank | Test weight lbs/bu | Heading days of yr | Plant height in | Lodging 0-9 | Winter stress (WS) 0-9 | Crown rust 0-9 | Stem rust 0-9 | BYDV 0-9 | Leafiness 0-9 |
|---|---|---|---|---|---|---|---|---|---|---|---|
| Gerard 224 | 108 | 3 | 32 | 101 | 41 | 2.3 | 2.7 | 7.0 | 5.0 | 1.5 | 4.2 |
| TAMO 411 | 103 | 7 | 34 | 103 | 42 | 2.2 | 2.6 | 7.0 | 6.0 | 0.4 | 4.3 |
| Horizon 201 | 103 | 8 | 31 | 100 | 48 | 4.2 | 3.3 | 5.0 | 1.0 | 1.0 | 3.3 |
| MEAN | 94 | | 33 | 100 | 45 | 3.0 | 4.7 | 3.2 | 1.7 | 0.6 | 5.5 |

WS: 0-9, 0 = none, 9 = severe.
Leafy Score: 0-9, 3 = very leafy, 8 = not much leaf biomass. Average of several ratings.
Lodging: 0 = none, 9 = severe.
Crown rust: 0 = none, 9 = severe.
Stem rust: 0 = none, 9 = severe.
BYDV: 0 = none, 9 = severe.
WS: 0 = none, 9 = severe.

TABLE 8

2014 Uniform Winter Oat data from Quincy, FL.

| Entry # | Variety | Pedigree | Yield (bu/ac) | Yield rank | TW (lbs/bu) | Growth habit | Forage Rating | Plant height (in) | Lodging | Crown Rust | Heading Date |
|---|---|---|---|---|---|---|---|---|---|---|---|
| 1 | Horizon 201 | FL92OHR35183-Y1/TX96M1384 (=FL99201-D29-E1) | 52 | 24 | 18.1 | 5 | 7 | 50 | 8 | 9 | 99 |
| 2 | LA99016 | TX96M1385/ SECTLA495 | 127 | 4 | 30.1 | 6 | 7 | 53 | 6 | 0 | 96 |
| 3 | Gerard 224 | Rodgers/Txab29923 // Rodgers (=NC03-2421v) | 50 | 25 | 19.3 | 6 | 5 | 49 | 3 | 9 | 100 |
| 4 | TAMO 411 | (=TX05CS347-1) | 63 | 21 | 24.0 | 7 | 5 | 46 | 3 | 8 | 100 |
| 5 | FL0720-R6 | FL0206FSB-34-S1/ FL06094 F1 (FL0016-H1/IL 3555) | 142 | 2 | 29.0 | 4 | 6 | 57 | 2 | 0 | 102 |
| Mean | | | 83.3 | | 26.1 | 5.6 | 5.5 | 50.3 | 3.8 | 5.2 | 98.3 |
| CV | | | 14.8 | | 7.8 | 4.3 | 5.0 | 4.5 | 10.6 | 5.7 | |
| LSD (0.1) | | | 16.8 | | 3.3 | 1.0 | 1.2 | 4.8 | 2.1 | 1.6 | |

Lodging: 0 = none, 9 = severe.
Growth Habit: 0-9 where 3 is very early, spring-like and 8 is very late, flat, winter.
Forage Rating: 0-9, 3 = less forage, 8 = very high leaf biomass. Average of several ratings.
Crown Rust: 0 = none, 9 = severe.

In 2014, FL0720 was included in the advanced silage testing trial (28 oat entries), which was planted in a replicated trial in Baton Rouge, La., and Quincy, Fla., and a forage silage trial in Marianna, Fla. Results from these trials are presented in Tables 8-9. FL0720 was ranked number one in the grain trial, while Horizon 201 was ranked 18. FL0720 also showed excellent crown rust and stem rust resistance. In the silage trial in Marianna, Fla., FL0720 produced 500 lbs/ac more forage (dry weight) than Horizon 201.

TABLE 9

Advance Silage data from Quincy, FL & Baton Rogue, LA, 2014.

| Brand/variety | ENT | Grain Yield bu/a | | | Test Wt lbs/bu | | | Seed Quality | Growth Habit 0-9 | | |
|---|---|---|---|---|---|---|---|---|---|---|---|
| | | LA | FL | Mean | LA | FL | Mean | LA | LA | FL | Mean |
| FL0720-R6 | 4 | 149.5 | 115.7 | 132.6 | 32.5 | 26.1 | 29.3 | 3.0 | 4.0 | 5.0 | 4.5 |
| Horizon 201 | 26 | 149.3 | 45.4 | 97.3 | 32.4 | 20.3 | 26.4 | 3.0 | 5.0 | 6.0 | 5.5 |
| Mean | | 126.1 | 78.2 | 102.1 | 31.1 | 29.0 | 30.0 | 3.2 | 3.4 | 5.4 | 4.4 |
| CV % | | 14.6 | | | 4.8 | | | 10.4 | | | |
| LSD(0.10) | | 37.7 | 12.0 | | 3.0 | 2.7 | | 0.7 | | | |

| Brand/variety | ENT | Leafiness 0-9 | | | Head Day of yr | | | HT FL | Lod FL | Crown Rust FL | Stem Rust LA | Phenotype LA |
|---|---|---|---|---|---|---|---|---|---|---|---|---|
| | | LA | FL | Mean | LA | FL | Mean | | | | | |
| FL0720-R6 | 4 | 3.8 | 3.0 | 3.4 | 100.0 | 100.0 | 100.0 | 57.0 | 6.0 | 0.0 | 2.0 | 5.1 |
| Horizon 201 | 26 | 4.2 | 4.0 | 4.1 | 99.3 | 98.0 | 98.7 | 53.0 | 9.0 | 9.0 | 3.5 | 4.7 |

TABLE 9-continued

Advance Silage data from Quincy, FL & Baton Rogue, LA, 2014.

| Mean | 4.7 | 3.4 | 4.1 | 94.8 | 94.8 | 94.8 | 50.7 | 3.8 | 0.2 | 1.8 | 5.1 |
|---|---|---|---|---|---|---|---|---|---|---|---|
| CV % | 11.4 | | 2.1 | | | | | | | 76.5 | 7.1 |
| LSD(0.10) | 0.9 | | 3.6 | | | | | | | ns | 0.8 |

Lodging: 0 = none, 9 = severe.
Leafy Score: 0-9, 3 = very leafy, 8 = not much leaf biomass.
Growth Habit: 0-9, 3 = very spring type, 8 = winter type.
Crown rust: 0-9, 0 = no crown rust, 9 = very susceptible to crown rust.
Stem rust: 0-9, 0 = no crown rust, 9 = very susceptible to crown rust.
Phenotype: visual appearance, 3 = excellent and 7 = poor.

TABLE 10

Advance Silage data from Marianna, FL Silage Trial.

| Entry | Designation | Pedigree | Silage (lb/ac) | Rank |
|---|---|---|---|---|
| 4 | FL0720-R6 | FL0206FSB-34-S1/FL06094 F1(FL0016-H1/IL 3555 (BYDV Res Line)) | 7752 | 13 |
| 26 | Horizon 201 | Check | 7226 | 22 |
| Mean | | | 7651 | |
| CV (%) | | | 10 | |
| LSD (0.1) | | | 1072 | |

Results from 3 locations of the 2014 Official Grain Variety Trials in Louisiana are presented in Tables 11-13. FL0720 performed very well in Baton Rouge and Bossier City, La., but not at Winnsboro, La. Crown rust was not a factor at these locations. It is noted that the lower yield of FL0720 in Winnsboro may be explained by the rather high lodging score. FL0720 was 7 days later in heading in Baton Rouge but only 3 days later in Winnsboro.

TABLE 11

Oat variety trial at Baton Rouge, LA in 2014.

| Brand/variety | Grain Yield bu/a | Test Weight lbs/bu | Seed Quality 0-9 | Leafiness 0-9 | Canopy Density 0-9 | Head Day of yr | Plant Ht in | Stem Rust 0-9 | Phenotype 0-9 |
|---|---|---|---|---|---|---|---|---|---|
| Horizon 201 | 170.5 | 32.6 | 4.3 | 4.3 | 4.0 | 97.3 | 47.5 | 2.0 | 5.3 |
| FL0720-R6 | 159.5 | 29.5 | 3.0 | 3.7 | 4.0 | 104.0 | 47.0 | 1.0 | 4.0 |
| LA99016 | 158.5 | 34.5 | 4.0 | 5.0 | 5.0 | 99.7 | 45.0 | 1.0 | 5.0 |
| HORIZON 306 | 153.6 | 33.3 | 4.3 | 3.7 | 4.3 | 101.3 | 40.5 | 2.0 | 4.0 |
| HORIZON 270 | 152.6 | 32.5 | 4.3 | 5.7 | 5.3 | 100.7 | 39.0 | 2.0 | 4.3 |
| BROOKS | 133.3 | 29.3 | 4.3 | 5.0 | 5.0 | 103.3 | 45.5 | 1.0 | 5.0 |
| REWG0913 | 113.5 | 34.4 | 3.3 | 5.0 | 5.0 | 105.0 | 41.5 | 2.0 | 5.2 |
| Mean | 139.8 | 32.5 | 4.3 | 5.2 | 5.1 | 99.2 | 42.3 | 1.1 | 4.8 |
| CV | 10 | 3 | 14 | 11 | 13 | 2 | 3 | | 14 |
| LSD | 23.4 | 1.9 | 1.0 | 1.0 | 1.1 | 2.8 | 2.9 | | 1.1 |

Lodging: 0 = none, 9 = severe.
Leafy Score: 0-9, 3 = very leafy, 8 = not much leaf biomass.
Canopy Density: 0-9, 3 = almost complete ground coverage, 8 = easily seed open spaces between rows.
Phenotype: visual appearance, 3 = excellent and 7 = poor.

TABLE 12

Oat variety trial at Winnsboro, LA in 2014.

| Brand/variety | Grain Yield bu/a | Test Weight lbs/bu | Head Day of yr | Plant Ht in | Lodging Score 0-9 | Growth Habit 0-9 | Freeze Damage 0-9 | Leafy Score 0-9 | Phenotype 0-9 | Bird Damage 0-9 |
|---|---|---|---|---|---|---|---|---|---|---|
| Horizon 201 | 142.0 | 34.6 | 105 | 51 | 7.3 | 4.0 | 1.7 | 2.5 | 3.6 | 0.7 |
| FL0720-R6 | 120.0 | 33.5 | 108 | 53 | 8.0 | 3.0 | 2.7 | 2.7 | 3.5 | 1.0 |
| LA99016 | 134.3 | 36.0 | 105 | 48 | 4.7 | 4.3 | 1.7 | 2.8 | 3.6 | 1.7 |
| HORIZON 270 | 167.7 | 34.9 | 104 | 42 | 3.3 | 4.3 | 1.3 | 4.3 | 4.0 | 1.7 |
| HORIZON 306 | 167.0 | 37.7 | 105 | 46 | 3.7 | 4.0 | 1.7 | 3.1 | 3.2 | 1.7 |
| BROOKS | 108.2 | 32.0 | 106 | 49 | 7.7 | 4.0 | 2.0 | 3.6 | 4.1 | 1.7 |
| REWG0913 | 110.5 | 38.0 | 105 | 44 | 7.3 | 5.0 | 2.0 | 4.4 | 4.9 | 1.7 |
| Mean | 130.7 | 34.9 | 103.1 | 46.2 | 4.8 | 4.0 | 2.2 | 4.0 | 4.2 | 1.8 |

TABLE 12-continued

Oat variety trial at Winnsboro, LA in 2014.

| Brand/variety | Grain Yield bu/a | Test Weight lbs/bu | Head Day of yr | Plant Ht in | Lodging Score 0-9 | Growth Habit 0-9 | Freeze Damage 0-9 | Leafy Score 0-9 | Pheno type 0-9 | Bird Damage 0-9 |
|---|---|---|---|---|---|---|---|---|---|---|
| CV | 10 | 2 | 1 | 4 | 35 | 13 | 28 | 9 | 6 | 41 |
| LSD (0.10) | 23.9 | 1.4 | 3.1 | 3.4 | 2.8 | 0.9 | 1.0 | 0.6 | 0.4 | NS |

Lodging: 0 = none, 9 = severe.
Growth Habit: 0-9 where 3 is very early, springlike and 8 is very late, flat, winter.
Freeze Damage: 0-9, 0 = none, 9 = severe.
Leafy Score: 0-9, 3 = very leafy, 8 = not much leaf biomass.
Phenotype: visual appearance, 3 = excellent and 7 = poor.
Bird Damage: 0 = none and 9 = complete. Bird damage occurred primarily on the front and back ranges and was not statistically significant.

TABLE 13

Oat variety trial in Bossier City, LA in 2014.

| Brand/variety | Grain* Yield bu/a | Test Weight lbs/bu | Head Day of yr | Plant Ht in |
|---|---|---|---|---|
| FL0720-R6 | 105.1 | 32.1 | 118 | 39 |
| Horizon 201 | 99.3 | 31.1 | 109 | 37 |
| LA99016 | 77.2 | 30.8 | 112 | 38 |
| HORIZON 306 | 91.1 | 34.2 | 117 | 38 |
| HORIZON 270 | 84.9 | 32.3 | 110 | 31 |
| BROOKS | 78.8 | 34.0 | 114 | 38 |
| REWG0913 | 93.0 | 31.0 | 114 | 34 |
| Mean | 79.2 | 31.5 | 111.8 | 35.7 |
| CV % | 18 | 5 | 2 | 10 |
| LSD (0.10) | 24.0 | 2.7 | 3.9 | 5.8 |

Results from 4 locations of the 2014 Official Grain Variety Trials in Georgia are presented in Tables 14-17. Of the 25 entries in these trials, FL0720 ranked number 1 for grain yield in Plains, number 6 in Midville, number 6 in Griffin, and number 16 in Calhoun compared to Horizon 201 at number 10 in Plains, number 16 in Midville, number 5 in Griffin, and number 1 in Calhoun. Crown rust was definitely a factor in Plains, and all of the standard varieties were susceptible at that location. FL0720 was scored as a zero for crown rust in Plains. Horizon 201 is very susceptibility to the new race of crown rust and its performance for grain yield is greatly affected by this disease. FL0720 was 6 days later in heading at Plains, 7 days later at Midville, 4 days later at Griffin, and 6 days at Calhoun.

TABLE 14

Oat Grain Performance in Plains, Georgia 2013-2014.

| Brand-Variety | Yield[1] 3-Year Average bu/acre | Yield[1] 2-Year Average bu/acre | 2014 Data Rank | Yield[1] bu/acre | Test Wt lb/bu | Ht in | Lodg. % | Head Date mo/day | Crown Rust[2] % |
|---|---|---|---|---|---|---|---|---|---|
| FL0720-R6 | • | • | 1 | 135.5 | 33.3 | 59 | 51 | 04/19 | 0 |
| Gerard 224 | 96.7 | 93.6 | 4 | 120.8 | 31.9 | 51 | 0 | 04/14 | 80 |
| Horizon 270 | 112.1 | 120.3 | 5 | 118.6 | 30.7 | 49 | 5 | 04/12 | 80 |
| Gerard 229 | 96.0 | 91.4 | 6 | 118.4 | 32.4 | 46 | 1 | 04/17 | • |
| Horizon 306 | 108.5 | 106.5 | 8 | 111.6 | 31.4 | 50 | 15 | 04/17 | 80 |
| Horizon 201 | 102.4 | 95.7 | 10 | 105.3 | 27.7 | 56 | 45 | 04/13 | 80 |
| SS 76-50 | 95.5 | 92.2 | 11 | 101.2 | 28.3 | 50 | 8 | 04/17 | 80 |
| NF27 | • | • | 23 | 70.7 | 27.8 | 62 | 48 | 04/12 | 80 |
| Okay | • | • | 24 | 60.0 | 26.7 | 51 | 94 | 04/19 | 80 |
| Average | 101.9 | 100.5 | | 99.5[3] | 30.4 | 52 | 24 | 04/14 | 60 |
| LSD at 10% Level | N.S.[3] | N.S. | | 11.9 | 1.8 | 2 | 22 | 01 | — |
| Std. Err. of Entry Mean | 3.9 | 5.3 | | 5.1 | 0.8 | 1 | 10 | 01 | — |

[1]Yields calculated as 32 pounds per bushel at 12.5% moisture.
[2]Crown rust data collected on May 13, 2014.
[3]C.V. = 10.2%, and df for EMS = 72.
[4] The F-test indicated no statistical difference at the alpha = 0.10 probability level; therefore, an LSD value was not calculated.

TABLE 15

Oat Grain Performance in Midville, Georgia 2013-2014.

| Brand-Variety | Yield[1] 3-Year Average bu/acre | Yield[1] 2-Year Average bu/acre | 2014 Data Rank | Yield[1] bu/acre | Test Wt lb/bu | Ht in | Lodg. % | Head Date mo/day |
|---|---|---|---|---|---|---|---|---|
| Gerard 229 | 106.2 | 103.0 | 1 | 144.8 | 35.6 | 46 | 3 | 04/17 |
| SS 76-50 | 100.5 | 90.7 | 3 | 110.7 | 32.9 | 44 | 38 | 04/15 |

TABLE 15-continued

Oat Grain Performance in Midville, Georgia 2013-2014.

| | Yield[1] | | | 2014 Data | | | | | |
| --- | --- | --- | --- | --- | --- | --- | --- | --- | --- |
| Brand-Variety | 3-Year Average bu/acre | 2-Year Average bu/acre | Rank | Yield[1] bu/acre | Test Wt lb/bu | Ht in | Lodg. % | Head Date mo/day | |
| Horizon 270 | 84.2 | 79.2 | 4 | 108.0 | 31.8 | 49 | 0 | 04/13 | |
| FL0720-R6 | • | • | 6 | 107.6 | 33.6 | 57 | 30 | 04/18 | |
| Gerard 224 | 95.1 | 86.4 | 8 | 105.9 | 33.4 | 50 | 41 | 04/16 | |
| Horizon 306 | 94.7 | 98.9 | 9 | 104.1 | 32.0 | 51 | 20 | 04/13 | |
| Horizon 201 | 85.4 | 87.5 | 16 | 85.6 | 27.1 | 51 | 45 | 04/11 | |
| Average | 94.4 | 90.8 | | 93.0 [2] | 31.2 | 51 | 22 | 04/14 | |
| LSD at 10% Level | N.S.[3] | N.S. | | 20.8 | 4.1 | 4 | 28 | 02 | |
| Std. Err. of Entry Mean | 4.8 | 6.1 | | 8.8 | 1.8 | 2 | 12 | 01 | |

[1]Yields calculated as 32 pounds per bushel at 12.5% moisture.
[2] C.V. = 19.0%, and df for EMS = 72.
[3]The F-test indicated no statistical difference at the alpha = 0.10 probability level; therefore, an LSD value was not calculated.

TABLE 16

Oat Grain Performance in Griffin, Georgia 2013-2014.

| | Yield[1] | | | 2014 Data | | | | | |
| --- | --- | --- | --- | --- | --- | --- | --- | --- | --- |
| Brand-Variety | 3-Year Average bu/acre | 2-Year Average bu/acre | Rank | Yield[1] bu/acre | Test Wt lb/bu | Ht in | Lodg. % | Head Date mo/day | Winter Survival % |
| Gerard 224 | 153.6 | 167.1 | 2 | 198.7 | 38.7 | 47 | 35 | 04/26 | 90 |
| SS 76-50 | 155.6 | 173.1 | 3 | 191.7 | 36.3 | 48 | 68 | 04/27 | 89 |
| Horizon 201 | 150.0 | 153.1 | 5 | 188.5 | 36.1 | 54 | 55 | 04/24 | 93 |
| FL0720-R6 | • | • | 6 | 187.2 | 38.6 | 54 | 90 | 04/28 | 90 |
| Horizon 270 | 160.6 | 180.0 | 7 | 186.2 | 36.9 | 46 | 33 | 04/26 | 93 |
| Horizon 306 | 151.9 | 160.3 | 10 | 181.7 | 39.1 | 47 | 60 | 04/28 | 93 |
| Gerard 229 | 144.7 | 162.7 | 11 | 181.0 | 37.1 | 43 | 18 | 04/29 | 90 |
| Average | 152.7 | 163.6 | | 168.8 [2] | 36.9 | 49 | 50 | 04/26 | 89 |
| LSD at 10% Level | N.S.[3] | N.S. | | 9.5 | 1.6 | 3 | 16 | 01 | 6 |
| Std. Err. of Entry Mean | 4.2 | 6.0 | | 4.1 | 0.7 | 1 | 7 | 01 | 3 |

[1]Yields calculated as 32 pounds per bushel at 12.5% moisture.
[2] C.V. = 8.2%, and df for EMS = 72.
[3]The F-test indicated no statistical difference at the alpha = 0.10 probability level; therefore, an LSD value was not calculated.

TABLE 17

Oat Grain Performance in Calhoun, Georgia 2013-2014.

| | Yield[1] | | | 2014 Data | | | | | |
| --- | --- | --- | --- | --- | --- | --- | --- | --- | --- |
| Brand-Variety | 3-Year Average bu/acre | 2-Year Average bu/acre | Rank | Yield[1] bu/acre | Test Wt lb/bu | Ht in | Lodg. % | Head Date mo/day | Winter Survival % |
| Horizon 201 | 120.6 | 124.1 | 1 | 185.1 | 34.6 | 53 | 96 | 04/21 | 100 |
| Horizon 270 | 98.1 | 116.1 | 2 | 171.8 | 36.7 | 43 | 88 | 04/23 | 100 |
| Gerard 229 | 108.1 | 125.6 | 4 | 162.7 | 34.6 | 42 | 96 | 04/25 | 100 |
| SS 76-50 | 112.6 | 120.3 | 5 | 162.4 | 35.9 | 48 | 99 | 04/21 | 100 |
| Horizon 306 | 101.4 | 110.2 | 6 | 160.7 | 40.1 | 48 | 98 | 04/23 | 100 |
| Gerard 224 | 99.6 | 99.5 | 9 | 140.7 | 36.5 | 47 | 96 | 04/21 | 100 |
| FL0720-R6 | • | • | 16 | 110.9 | 32.2 | 53 | 100 | 04/27 | 100 |
| Average | 106.7 | 108.6 | | 126.7 [2] | 33.8 | 48 | 92 | 04/22 | 88 |
| LSD at 10% Level | N.S.[3] | N.S. | | 15.7 | 1.4 | 3 | 12 | 02 | 9 |
| Std. Err. of Entry Mean | 6.0 | 7.0 | | 10.0 | 0.6 | 1 | 5 | 01 | 4 |

[1]Yields calculated as 32 pounds per bushel at 12.5% moisture.
[2] C.V. = 15.7%, and df for EMS = 72.
[3]The F-test indicated no statistical difference at the alpha = 0.10 probability level; therefore, an LSD value was not calculated.

FL0720 was also included in Oat Variety Performance Trials in South Carolina and Texas. This oat variety trial was planted in two locations (Blackville and Florence) in South Carolina (Tables 18-19). FL0720 performed very well at Blackville and Florence. Crown rust was not a factor at these locations. Summary data of South Texas regional trial is presented in Table 20. This regional trial is comprised of three locations Castroville, Uvalde, and Wharton. Overall performance of FL0720 and Horizon 201 are similar, but FL0720 showed excellent performance in Uvalde. Data from the North Texas locations are not presented because of cold damage to many of the entries.

TABLE 18

Oat Variety Performance Trials in Blackville, SC.

| Variety | Yield Bu/Ac | Test Wt lb/bu | Pl Ht Inch |
|---|---|---|---|
| HORIZON 201 | 132.9 | 33.2 | 39 |
| GERARD 224 | 130.8 | 34.3 | 35 |
| FL0720-R6 | 127.1 | 33.3 | 42 |
| GRAHAM | 126.5 | 33.3 | 31 |
| GERARD 229 | 113.0 | 32.1 | 30 |
| SIMPSON | 108.7 | 33.3 | 37 |

TABLE 18-continued

Oat Variety Performance Trials in Blackville, SC.

| Variety | Yield Bu/Ac | Test Wt lb/bu | Pl Ht Inch |
|---|---|---|---|
| HORIZON 270 | 106.2 | 34.4 | 32 |
| HORIZON 306 | 94.5 | 33.1 | 32 |
| AVERAGES | 111.6 | 34.2 | 36 |
| L.S.D. (.10) | 16.2 | 0.9 | |
| C.V. (%) | 10.6 | 1.8 | |
| STD. ERROR OF ENTRY MEAN | 6.8 | DF = 46 | |

TABLE 19

Oat Variety Performance Trials in Florence, SC.

| | Yield Bu/Ac | Test Wt lb/bu | Pl Ht Inch | 50% heading date |
|---|---|---|---|---|
| FL0720-R6 | 96.8 | 31.8 | 41 | 4/29 |
| HORIZON 201 | 96.3 | 33.7 | 41 | 4/23 |
| AVERAGES | | 33.8 | 38 | 4/25 |
| L.S.D. (.10) | 1.8 | | | |
| C.V. (%) | 1.3 | | | |
| STD. ERROR OF ENTRY MEAN | DF = 46 | | | |

TABLE 20

2014 Uniform Oat Variety Trial, South Texas Regional Summary.

| Regional rank | Variety | Developer | Yield (bu/ac) | | | | Test Wt (lb/bu) |
|---|---|---|---|---|---|---|---|
| | | | Average | Castroville | Uvalde | Wharton | 2014 |
| 9 | RAM 99016 | LSU | 83.3 | 88.8 | 65.8 | 90.5 | 34.0 |
| 11 | Horizon 306 | LSU | 80.2 | 77.9 | 79.0 | 85.0 | 32.3 |
| 13 | TAMO 411 | TAMU | 77.6 | 83.8 | 66.9 | 79.4 | 32.3 |
| 14 | Horizon 270 | UF | 74.5 | 84.2 | 44.8 | 84.6 | 32.3 |
| 15 | TAMO 406 | TAMU | 73.9 | 76.8 | 77.6 | 70.0 | 33.0 |
| 17 | Horizon 201 | UF | 73.5 | 73.2 | 54.4 | 86.7 | 30.3 |
| 18 | FL0720-R6 | UF | 72.2 | 74.2 | 103.1 | 51.9 | 28.7 |
| 20 | Bob | UA | 67.2 | 74.6 | 90.6 | 45.5 | 32.0 |
| 21 | Nora | UA | 63.4 | 62.4 | 64.3 | 64.2 | 31.7 |
| 22 | Dallas | TAMU | 62.5 | 66.8 | 69.6 | 54.7 | 29.0 |
| 23 | TAMO 606 | TAMU | 61.4 | 67.8 | 51.9 | 62.4 | 29.7 |
| 29 | OKAY | Noble Foundation | 45.1 | 35.8 | 69.8 | 39.3 | 26.7 |
| 30 | NF-27 | Noble Foundation | 45.0 | 35.9 | 46.9 | 53.2 | 28.0 |
| | LSD (5%) | | 12.7 | 21.6 | 31.7 | 18.6 | 3.7 |
| | CV (%) | | 17.7a | 17.7a | 20.8a | 15.9a | 7.2 |
| | Mean | | 73.0 | 74.6 | 74.6 | 71.4 | 31.1 | aTrials with a coefficient of variation (CV) ≥ 15% contain excessive experimental error. Readers should consider trials in a similar environment to confirm varietal effect on yields.

2014 was the first year that FL0720 had been evaluated for forage production. Part of the testing includes clipping trials conducted at several locations including Marianna, Fla. Results of those trials are presented in Tables 20-23. 2014 was a very cold winter with several periods with extremely low temperatures and cold damage occurred on many oats. FL0720 performed well at the first clipping at each site and was above the test average at all 4 locations. It was apparently damaged by low temperatures and did not perform as well for the subsequent clippings at all 3 of the Georgia locations (Tables 21-23), and was above the test average at the Marianna, Fla. location for season total forage production (Table 24).

TABLE 21

Oat Forage Performance in Plains, Georgia 2013-2014.

| | Dry Matter Yield | | | | |
|---|---|---|---|---|---|
| | Harvest Date | | | Season Totals | |
| Variety | Jan. 23, 2014 | Feb. 25, 2014 | Apr. 1, 2014 | 2014 | 2-Yr Avg |
| | | | lb/acre | | |
| RAM LA99016 | 2439 | 1089 | 2552 | 6080 | 6155 |
| FL0720-R6 | 2287 | 512 | 2420 | 5219 | . |
| Average | 1933 | 1040 | 2513 | 5486[1] | 5726 |
| LSD at 10% Level | 335 | 323 | 469 | 498 | 319 |
| Std. Err. of Entry Mean | 142 | 136 | 198 | 210 | 179 |

[1]C.V. = 7.7%, and df for EMS = 57.

TABLE 22

Oat Forage Performance in Tifton, Georgia 2013-2014.

| | Dry Matter Yield | | | | | |
|---|---|---|---|---|---|---|
| | | | | | Season Totals | |
| | Harvest Date | | | | | 2-Yr |
| Variety | Dec. 11, 2013 | Feb. 6, 2014 | Mar. 11, 2014 | Apr. 11, 2014 | 2014 | Avg |
| | | | lb/acre | | | |
| RAM LA99016 | 1601 | 1590 | 2639 | 3234 | 9064 | 7341 |
| FL0720-R6 | 1982 | 1318 | 2396 | 2625 | 8320 | . |
| Average | 1846 | 1414 | 2585 | 2816 | 8662[1] | 7614 |
| LSD at 10% Level | 317 | 171 | 461 | 278 | 578 | 404 |
| Std. Err. of Entry Mean | 134 | 72 | 195 | 118 | 244 | 167 |

[1]C.V. = 5.6%, and df for EMS = 57.

TABLE 23

Oat Forage Performance in Tifton, Georgia 2013-2014.

| | Dry Matter Yield | | | | Cold | Plant |
|---|---|---|---|---|---|---|
| | Harvest Date | | Season Totals | | | |
| | Mar. 11, 2014 | Apr. 11, 2014 | 2014 | 2-Yr Avg | Damage[1] | Stand[2] |
| Variety | | lb/acre | | | % | % |
| RAM LA99016 | 1726 | 3264 | 4990 | 11642 | 33 | 15 |
| FL0720-R6 | 1864 | 2280 | 4144 | . | 66 | 13 |
| Average | 1567 | 2947 | 4514 [3] | 10599 | 42 | 22 |
| LSD at 10% Level | 583 | 652 | 628 | N.S.[4] | — | — |
| Std. Err. of Entry Mean | 247 | 276 | 266 | 413 | — | — |

[1]C.V. = 5.6%, and df for EMS = 57.

TABLE 24

Oat Forage Performance in Marianna, Georgia 2013-2014.

| | Dry Matter Yield | | | | | |
|---|---|---|---|---|---|---|
| | Harvest Date | | | | Season Totals | |
| Brand-Variety | Jan. 27, 2014 | Feb. 25, 2014 | Mar. 28, 2014 lb/acre | Apr. 28, 2014 | 2014 | 2-Yr Avg |
| RAM LA99016 | 92 | 1585 | 3888 | 572 | 6136 | 5627 |
| FL0720-R6 | 821 | 1369 | 2596 | 952 | 5738 | • |
| Cosaque* | 263 | 1250 | 3102 | 632 | 5247 | • |
| Average | 361 | 1342 | 3256 | 713 | 5672 [1] | 5948 |
| LSD at 10% Level | 184 | N.S.[2] | 336 | 212 | 466 | N.S. |
| Std. Err. of Entry Mean | 78 | 101 | 142 | 90 | 197 | 147 |

[1] C.V. = 6.9%, and df for EMS = 54.
[2] The F-test indicated no statistical difference at the alpha = 0.10 probability level; therefore an LSD value was not calculated.

FL0720 oat showed full maturity and excellent disease resistance, particularly resistance to a new race of crown rust that attacks all currently available varieties. It also has excellent grain yield potential, good test weight, and good early season forage production. There is demand for such a variety, and the line could serve well for forage, grain, cover, and wildlife food plot uses.

Further Embodiments of the Invention

The invention also provides seed of a plant of the invention. The oat seed of the invention may or may not be provided as an essentially homogeneous population of oat seed. Essentially homogeneous populations of seed are generally free from substantial numbers of other seed. Therefore, a seed of the invention may, in one embodiment, be defined as forming at least about 97% of the total seed, including at least about 98%, 99%, or more of the seed. In certain embodiments, the population of oat seed may be particularly defined as being essentially free from hybrid seed. The seed population may be separately grown to provide an essentially homogeneous population of oat plants.

As used herein, "oat plant" also includes plants modified to include at least a first desired heritable trait. Such plants may, in one embodiment, be developed by a plant breeding technique called backcrossing, wherein essentially all of the desired morphological and physiological characteristics of a variety are recovered, in addition to a genetic locus transferred into the plant via the backcrossing technique. The term "single locus converted plant" as used herein refers to those oat plants which are developed by a plant breeding technique called backcrossing, wherein essentially all of the desired morphological and physiological characteristics of a variety are recovered in addition to the single locus transferred into the variety via the backcrossing technique.

Introgression of a desired trait into a plant according to the present invention may be accomplished by any methods known in the art. For example, marker-assisted introgression may involves the transfer of a chromosomal region, defined by one or more markers, from one plant or germplasm to a second plant or germplasm. Offspring of a cross that contain the introgressed genomic region can be identified by the combination of markers characteristic of the desired introgressed genomic region from a first germplasm (e.g., a plant or germplasm having a desired trait or phenotype) and both linked and unlinked markers characteristic of the desired genetic background of a second germplasm.

Backcrossing methods can be used with the present invention to improve or introduce a characteristic into the present variety. The parental oat plant that contributes the locus for the desired characteristic is termed the nonrecurrent or donor parent. This terminology refers to the fact that the nonrecurrent parent is used one time in the backcross protocol and therefore does not recur. The parental oat plant to which the locus or loci from the nonrecurrent parent are transferred is known as the recurrent parent, as it is used for several rounds in the backcrossing protocol.

In a typical backcross protocol, the original variety of interest (recurrent parent) is crossed to a second variety (nonrecurrent parent) that carries the single locus of interest to be transferred. The resulting progeny from this cross are then crossed again to the recurrent parent, and the process is repeated until an oat plant is obtained wherein essentially all of the desired morphological and physiological characteristics of the recurrent parent are recovered in the converted plant, in addition to the single transferred locus from the nonrecurrent parent.

The selection of a suitable recurrent parent is an important step for a successful backcrossing procedure. The goal of a backcross protocol is to alter or substitute a single trait or characteristic in the original variety. To accomplish this, a single locus of the recurrent variety is modified or substituted with the desired locus from the nonrecurrent parent, while retaining essentially all of the rest of the desired genetic material and therefore the desired physiological and morphological constitution of the original variety. The choice of the particular nonrecurrent parent will depend on the purpose of the backcross; one of the major purposes is to add some commercially desirable trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

In one embodiment, progeny oat plants of a backcross in which oat variety FL0720 is the recurrent parent comprise (i) the desired trait from the non-recurrent parent and (ii) all of the physiological and morphological characteristics of a plant of the invention as determined at the 5% significance level when grown in the same environmental conditions.

Oat varieties can also be developed from more than two parents. The technique, known as modified backcrossing, uses different recurrent parents during the backcrossing. Modified backcrossing may be used to replace the original recurrent parent with a variety having certain more desirable characteristics, or multiple parents may be used to obtain different desirable characteristics from each.

Many single locus traits have been identified that are not regularly selected for in the development of a new inbred but that can be improved by backcrossing techniques. Single locus traits may or may not be transgenic; examples of these traits include, but are not limited to, male sterility, herbicide tolerance, resistance to bacterial, fungal, or viral disease, insect resistance, restoration of male fertility, modified fatty acid or carbohydrate metabolism, and enhanced nutritional quality. These traits comprise genes generally inherited through the nucleus.

Direct selection may be applied where the single locus acts as a dominant trait. An example of a dominant trait is the anthracnose resistance trait. For this selection process, the progeny of the initial cross are sprayed with anthracnose spores prior to the backcrossing. The spraying eliminates any plants that do not have the desired anthracnose resistance characteristic, and only those plants which have the anthracnose resistance gene are used in the subsequent backcross. This process is then repeated for all additional backcross generations.

Selection of oat plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross, and can be used in selection of progeny for continued breeding. This technique is commonly referred to as marker-assisted selection. Any other type of genetic marker or other assay which is able to identify the relative presence or absence of a trait of interest in a plant can also be useful for breeding purposes. Procedures for marker-assisted selection applicable to the breeding of oats are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

Plants Derived by Genetic Engineering

Many useful traits that can be introduced by backcrossing, as well as directly into a plant, are those which are introduced by genetic transformation techniques. Genetic transformation may therefore be used to insert a selected transgene into the oat variety of the present invention, and/or a parent of a hybrid oat variety produced according to the invention, or may, alternatively, be used for the preparation of transgenes that can be introduced by backcrossing. Methods for the transformation of plants, including oats, are well known to those of skill in the art.

Most research efforts have been directed at developing Agrobacterium-mediated transformation methods with relatively little emphasis on direct gene transfer techniques. Procedures for the transformation of A. sativa would be known to one of skill in the art. Principal difficulties in such techniques may relate to combining efficient plant regeneration with gene transfer. Inefficient selection can result in the regeneration of chimeric plants upon Agrobacterium tumefaciens-mediated transformation. Promising results have been obtained with Agrobacterium rhizogenes-mediated transformation. Few agronomically useful characters have been introduced, the majority of research having been confined to the introduction of marker and reporter genes.

Generally speaking, techniques that may be employed for the genetic transformation of oat include, but are not limited to, electroporation, microprojectile bombardment, Agrobacterium-mediated transformation and direct DNA uptake by protoplasts.

To effect transformation by electroporation, one may employ either friable tissues, such as a suspension culture of cells or embryogenic callus, or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

A particularly efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target oat cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

Microprojectile bombardment techniques are widely applicable, and may be used to transform virtually any plant species.

Agrobacterium-mediated transfer is another widely applicable system for introducing gene loci into plant cells. An advantage of the technique is that DNA can be introduced into whole plant tissues, thereby bypassing the need for regeneration of an intact plant from a protoplast. Modern Agrobacterium transformation vectors are capable of replication in E. coli as well as Agrobacterium, allowing for convenient manipulations (Klee et al., 1985). Moreover, recent technological advances in vectors for Agrobacterium-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, Agrobacterium containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., 1985; U.S. Pat. No. 5,563,055).

Transformation of plant protoplasts also can be achieved using methods based on calcium phosphate precipitation, polyethylene glycol treatment, electroporation, and combinations of these treatments (see, e.g., Potrykus et al., 1985; Omirulleh et al., 1993; Fromm et al., 1986; Uchimiya et al., 1986; Marcotte et al., 1988). Transformation of plants and expression of foreign genetic elements is exemplified in Choi et al. (1994), and Ellul et al. (2003).

A number of promoters have utility for plant gene expression for any gene of interest including, but not limited to, selectable markers, scoreable markers, genes for pest tolerance, disease resistance, nutritional enhancements, and any other gene of agronomic interest. Examples of constitutive promoters useful for oat plant gene expression include, but are not limited to, the cauliflower mosaic virus (CaMV) P-35S promoter, which confers constitutive, high-level expression in most plant tissues (see, e.g., Odel et al., 1985), including monocots (see, e.g., Dekeyser et al., 1990; Terada and Shimamoto, 1990); a tandemly duplicated version of the CaMV 35S promoter, the enhanced 35S promoter (P-e35S) the nopaline synthase promoter (An et al., 1988), the octopine synthase promoter; and the figwort mosaic virus (P-FMV) promoter as described in U.S. Pat. No. 5,378,619 and an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, and other plant DNA virus promoters known to express in plant cells.

A variety of plant gene promoters that are regulated in response to environmental, hormonal, chemical, and/or developmental signals can be used for expression of an operably linked gene in plant cells, including promoters regulated by (1) heat (Callis et al., 1988), (2) light (e.g., pea rbcS-3A promoter, Kuhlemeier et al., 1989; maize rbcS promoter, Schaffner and Sheen, 1991; or chlorophyll a/b-binding protein promoter, Simpson et al., 1985), (3) hormones, such as abscisic acid (Marcotte et al., 1989), (4) wounding (e.g., wun1, Siebertz et al., 1989); or (5) chemicals such as methyl jasmonate, salicylic acid, or Safener. It may also be advantageous to employ organ-specific promoters (e.g., Roshal et al., 1987; Schernthaner et al., 1988; Bustos et al., 1989).

Exemplary nucleic acids which may be introduced to the oat variety of this invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into an oat plant according to the invention. Non-limiting examples of particular genes and corresponding phenotypes one may choose to introduce into an oat plant include one or more genes for insect tolerance, such as a *Bacillus thuringiensis* (Bt) gene, pest tolerance such as genes for fungal disease control, herbicide tolerance such as genes conferring glyphosate tolerance, and genes for quality improvements such as yield, nutritional enhancements, environmental or stress tolerances, or any desirable changes in plant physiology, growth, development, morphology or plant product(s). For example, structural genes would include any gene that confers insect tolerance including, but not limited to, a *Bacillus* insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference it their entirety. In another embodiment, the structural gene can confer tolerance to the herbicide glyphosate as conferred by genes including, but not limited to *Agrobacterium* strain CP4 glyphosate tolerant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., 1991). The RNA could also be a catalytic RNA molecule (i.e., a ribozyme) engineered to cleave a desired endogenous mRNA product (see, for example, Gibson and Shillito, 1997). Thus, any gene that produces a protein or mRNA that expresses a phenotype or morphology change of interest is useful for the practice of the present invention.

Definitions

In the description and tables herein, a number of terms are used. In order to provide a clear and consistent understanding of the specification and claims, the following definitions are provided:

Allele: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny, for example a first generation hybrid ($F_1$), back to one of the parents of the hybrid progeny. Backcrossing can be used to introduce one or more single locus conversions from one genetic background into another.

Crossing: The mating of two parent plants.

Cross-pollination: Fertilization by the union of two gametes from different plants.

Diploid: A cell or organism having two sets of chromosomes.

Emasculate: The removal of plant male sex organs or the inactivation of the organs with a cytoplasmic or nuclear genetic factor conferring male sterility or a chemical agent.

$F_1$ Hybrid: The first generation progeny of the cross of two nonisogenic plants.

Genotype: The genetic constitution of a cell or organism.

Haploid: A cell or organism having one set of the two sets of chromosomes in a diploid.

Linkage: A phenomenon wherein alleles on the same chromosome tend to segregate together more often than expected by chance if their transmission was independent.

Marker: A readily detectable phenotype, preferably inherited in codominant fashion (both alleles at a locus in a diploid heterozygote are readily detectable), with no environmental variance component, i.e., heritability of 1.

Phenotype: The detectable characteristics of a cell or organism, the characteristics of which are the manifestation of gene expression.

Quantitative Trait Loci (QTL): Quantitative trait loci (QTL) refer to genetic loci that control to some degree numerically representable traits that are usually continuously distributed.

Regeneration: The development of a plant from tissue culture.

Resistance: As used herein, the terms "resistance" and "tolerance" are used interchangeably to describe plants that show no symptoms to a specified biotic pest, pathogen, abiotic influence, or environmental condition. These terms are also used to describe plants showing some symptoms but that are still able to produce marketable product with an acceptable yield. Some plants that are referred to as resistant or tolerant are only so in the sense that they may still produce a crop, even though the plants are stunted and the yield is reduced.

Self-pollination: The transfer of pollen from the anther to the stigma of the same plant.

Single Locus Converted (Conversion) Plant: Plants that are developed by a plant breeding technique called backcrossing, wherein essentially all of the desired morphological and physiological characteristics of an oat variety are recovered in addition to the characteristics of the single locus transferred into the variety via the backcrossing technique and/or by genetic transformation.

Substantially Equivalent: A characteristic that, when compared, does not show a statistically significant difference (e.g., p=0.05) from the mean.

Tissue Culture: A composition comprising isolated cells of the same or a different type or a collection of such cells organized into parts of a plant.

Transgene: A genetic locus comprising a sequence that has been introduced into the genome of an oat plant by transformation.

Any embodiment discussed herein with respect to one aspect of the invention applies to other aspects of the invention as well, unless specifically noted.

The term "about" is used to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When used in conjunction with the word "comprising" or other open language in the claims, the words "a" and "an" denote "one or more," unless specifically noted. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

All references cited herein are hereby expressly incorporated herein by reference.

DEPOSIT INFORMATION

Deposit of oat variety FL0720, which is disclosed above and recited in the claims, was made with the American Type Culture Collection (ATCC), 10801 University Blvd., Manassas, Va. 20110-2209. The date of deposit is Nov. 9, 2017 and the accession number for the deposited seeds is ATCC Accession No. PTA-124569. Upon issuance of a patent, all restrictions upon the deposits will be removed, and the deposits are intended to meet all of the requirements of 37 C.F.R. § 1.801-1.809. The deposits will be maintained in the depository for a period of 30 years, or 5 years after the last request, or for the effective life of the patent, whichever is longer, and will be replaced if necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. A plant of oat variety FL0720, wherein a sample of seed of said variety has been deposited under ATCC Accession No. PTA-124569.

2. A plant part of the plant of claim 1, wherein the plant part comprises at least one cell of said plant.

3. The plant part of claim 2, further defined as pollen, a meristem, a cell, a seed, or an ovule.

4. A seed that produces the plant of claim 1.

5. A method of producing oat seed, wherein the method comprises crossing the plant of claim 1 with itself or a second oat plant.

6. The method of claim 5, wherein the method is further defined as comprising crossing the plant of oat variety FL0720 with a second, distinct oat plant to produce an F1 hybrid oat seed.

7. An F1 hybrid oat seed produced by the method of claim 6.

8. An F1 hybrid oat plant produced by growing the seed of claim 7.

9. A composition comprising the seed of claim 4 comprised in plant seed growth media, wherein a sample of seed of said variety has been deposited under ATCC Accession No. PTA-124569.

10. The composition of claim 9, wherein the growth media is soil or a synthetic cultivation medium.

11. A plant of oat variety FL0720, further comprising a single locus conversion, wherein a sample of seed of oat variety FL0720 has been deposited under ATCC Accession No. PTA-124569.

12. The plant of claim 11, wherein the single locus conversion comprises a transgene.

13. A seed that produces the plant of claim 11.

14. The seed of claim 13, wherein the single locus confers a trait selected from the group consisting of male sterility, herbicide tolerance, insect resistance, pest resistance, disease resistance, modified fatty acid metabolism, abiotic stress resistance, altered seed amino acid composition, site-specific genetic recombination, and modified carbohydrate metabolism.

15. The seed of claim 14, wherein the single locus confers tolerance to an herbicide selected from the group consisting of glyphosate, sulfonylurea, imidazolinone, dicamba, glufosinate, phenoxy propionic acid, L-phosphinothricin, cyclohexanone, cyclohexanedione, triazine, and benzonitrile.

16. The seed of claim 13, wherein the single locus conversion comprises a transgene.

17. The method of claim 6, wherein the method further comprises:
(a) crossing a plant grown from said F1 hybrid oat seed with itself or a different oat plant to produce a seed of a progeny plant of a subsequent generation;
(b) growing a progeny plant of a subsequent generation from said seed of the progeny plant of a subsequent generation and crossing the progeny plant of the subsequent generation with itself or a second plant to produce a progeny plant of a further subsequent generation; and
(c) repeating steps (a) and (b) using said progeny plant of a further subsequent generation from step (b) in place of the plant grown from said F1 hybrid oat seed in step (a), wherein steps (a) and (b) are repeated with sufficient inbreeding to produce an inbred oat plant derived from the oat variety FL0720.

18. A method of producing a commodity plant product comprising collecting the commodity plant product from the plant of claim 1.

19. A method of producing a progeny oat plant comprising applying plant breeding techniques to the plant of claim 1 or an F1 hybrid thereof to yield said progeny oat plant.

20. The method of claim 19, wherein the plant breeding techniques comprise backcrossing, marker assisted breeding, pedigree breeding, selfing, outcrossing, haploid production, doubled haploid production, or transformation.

* * * * *